United States Patent [19]
Chandler

[11] Patent Number: 5,468,229
[45] Date of Patent: Nov. 21, 1995

[54] PERITONEAL DIALYSIS CATHETER SUPPORT BELT

[76] Inventor: Janice Chandler, 287 Moore St., Greenville, S.C. 29605

[21] Appl. No.: 333,254

[22] Filed: Nov. 2, 1994

[51] Int. Cl.⁶ ............................................... A61M 25/02
[52] U.S. Cl. .................... 604/179; 128/DIG. 26
[58] Field of Search ................... 604/174, 179; 128/DIG. 26

[56] References Cited

U.S. PATENT DOCUMENTS

| | | |
|---|---|---|
| 3,059,645 | 10/1962 | Hasbrouck et al. ............... 604/179 |
| 4,088,136 | 5/1978 | Hasslinger et al. ............... 604/178 |
| 4,316,461 | 2/1982 | Marais et al. .................... 128/DIG. 26 |
| 4,453,933 | 6/1984 | Speaker ........................... 604/179 |
| 4,578,062 | 3/1986 | Schneider . | 
| 4,582,508 | 4/1986 | Pavelka . |
| 4,596,560 | 6/1996 | Simpson .......................... 604/174 |
| 4,666,432 | 5/1987 | McNeish et al. . |
| 4,738,661 | 4/1988 | Marut ............................. 128/DIG. 26 |
| 4,844,061 | 7/1989 | Carroll ............................ 604/179 |
| 4,955,867 | 9/1990 | Endo . |
| 4,959,055 | 9/1990 | Hillyer . |
| 5,037,397 | 8/1991 | Kalt et al. . |
| 5,048,512 | 9/1991 | Turner et al. .................... 604/179 |
| 5,244,464 | 9/1993 | Madden et al. . |
| 5,304,145 | 4/1994 | Blair .............................. 604/179 |
| 5,342,317 | 8/1994 | Claywell . |

Primary Examiner—Paul J. Hirsch
Attorney, Agent, or Firm—Haradaway Law Firm

[57] ABSTRACT

A recloseable belt for a peritoneal dialysis patient having an aperture for receiving and orienting the protruding portion of an implanted catheter toward a plurality of holders along one portion of the belt.

10 Claims, 1 Drawing Sheet

PERITONEAL DIALYSIS CATHETER SUPPORT BELT

BACKGROUND OF THE INVENTION

This invention relates generally to the art of body garments for securing and supporting a surgically implanted catheter, and particularly to a belt for securing and supporting an implanted catheter at the site of peritoneal dialysis therapy.

A surgically implanted catheter provides an opening through which dialysis solution can be instilled into the abdominal cavity of a peritoneal dialysis patient. Since free movement of the external portion of the catheter can cause irritation and infection at the exit site, the protruding catheter needs to be secured against the patient's body, thus providing greater protection and comfort.

Various body garments exist in the prior art for securing and supporting medical tubing and catheters. U.S. Pat. Nos. 4,666,432 to McNeil, 4,582,508 to Pavelka, and 4,578,062 to Schneider disclose garments with over-the-shoulder straps which secure a catheter to the upper body torso. In U.S. Pat. Nos. 5,244,464 to Madden et al. and 5,342,317 to Claywell, an anchor band is fastened to a portion of the body, medical tubing traverses the band, and a secondary band or strip secures the tubing to the anchor band. U.S. Pat. Nos. 4,959,055 to Hillyer discloses a retainer for a percutaneous tube which provides a seal to prevent the loss of fluids through the exit site, and U.S. Pat. No. 5,037,397 to Kalt et al. discloses a clamp which holds medical tubing to the skin of a patient.

U.S. Pat. No. 4,955,867 to Endo discloses a peritoneal dialysis catheter protector belt equipped with an open-ended pouch which protects the end of the catheter and prevents it from dangling. The belt is displaced slightly from the protruding end of the catheter at the exit site, such that the catheter passes over the belt in order for its end to be received by the pouch. There is no teaching by the patent of direct support at the exit site for the catheter, and no teaching of providing an initial orientation to the protruding catheter in order to direct it to the pouch.

In current practice, many peritoneal dialysis patients use adhesive tape to maintain the external portion of the catheter against the body so that it does not hang and is not otherwise susceptible to inadvertent dislodgement. The tape secures the catheter directly to the skin. In order to have therapeutic access to the protruding end of the catheter, however, the tape must be removed, then reapplied upon completing the dialysis procedure. The repeated application and removal of the adhesive material can cause the skin to become sensitive and irritated, particularly in elderly patients, which may induce intense pain and anxiety in the patient.

While the prior art may satisfactorily provide for the needs of many peritoneal dialysis patients, room exists for improvement in providing a belt which directly supports the protruding catheter at the exit site, orients the catheter toward the holding means along the belt, and supports the catheter along its entire protruding length. It is also important and advantageous that such belt not employ the use of adhesive materials.

SUMMARY OF THE INVENTION

It is therefore an object of the present invention to provide a peritoneal dialysis catheter belt which overcomes the limitations of the prior art.

It is a another object of the present invention to provide a peritoneal dialysis catheter belt which defines an opening therein for receipt and orientation of a peritoneal catheter toward a series of holders along the belt.

It is a further object of the present invention to provide a peritoneal dialysis catheter belt which allows for maximum freedom of bodily movement while maintaining the proper orientation of the catheter at the exit site.

It is a still further object of the present invention to provide a peritoneal dialysis catheter belt which accommodates any size or length .catheter and which can accommodate any size patient.

It is a still further object of the present invention to provide a peritoneal dialysis catheter belt which eliminates the use of adhesive material.

It is a still further object of the present invention to provide a peritoneal dialysis catheter belt of simple construction that is easily and economically manufactured.

These as well as other objects are accomplished by a belt for a peritoneal dialysis patient comprising an inner surface and an outer surface, a first end which is reversibly securable to a second end by securing means, an aperture defined by the belt, and a plurality of holders immediately adjacent the aperture along one portion of the belt's outer surface. The belt secures and supports the entire external portion of a peritoneal catheter which extends from the exit site on the patient's body and projects through the aperture defined by the belt to be oriented toward and secured by the holders.

DETAILED DESCRIPTION

In accordance with this invention, it has been found that a catheter support belt may be provided for a peritoneal dialysis patient such that it receives the catheter through an aperture thereon and orients the catheter towards a series of holders along the belt. The reinforced aperture supports the catheter at the exit site on the body. The catheter is held securely by a plurality of holders which accommodates its specific size and length. Various other advantages and features will become apparent from a reading of the following description which is given with reference to the figures of drawing.

Figure 1:
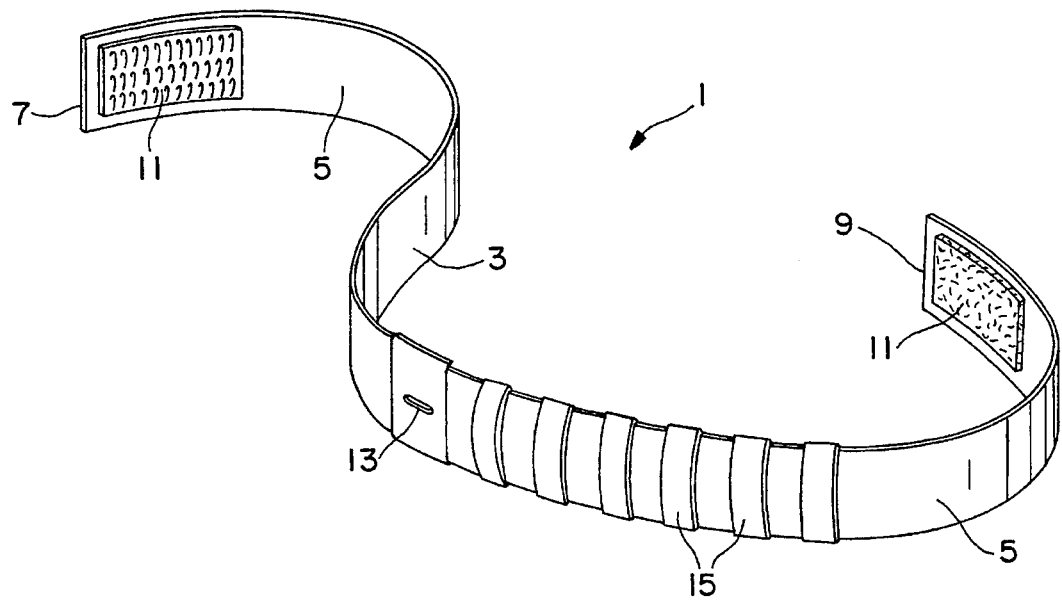
FIG. 1 of the drawings is a perspective view of a peritoneal dialysis catheter support belt in accordance with the present invention.
Figure 2:
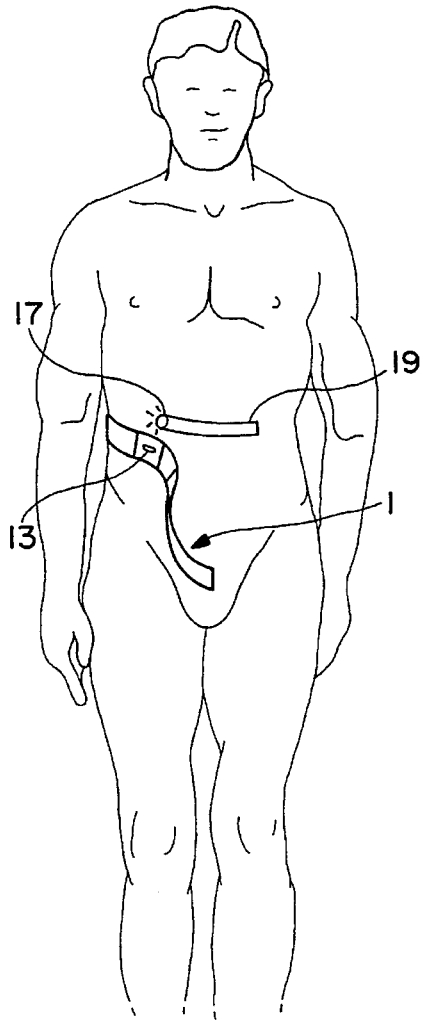
FIG. 2 of the drawings is an elevational view showing the alignment of the belt aperture with the exit site on the body in accordance with the present invention.
Figure 3:
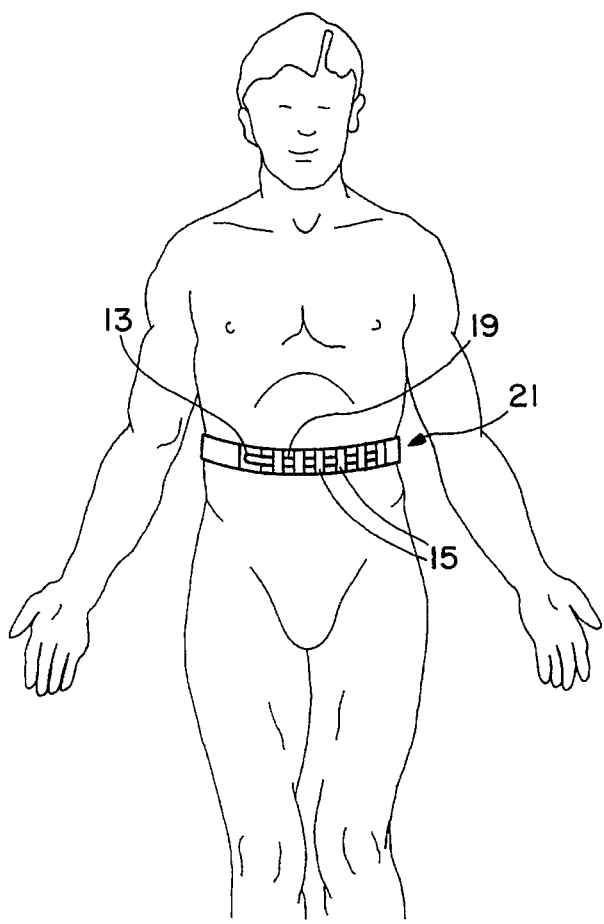
FIG. 3 of the drawings is an elevational view of a peritoneal dialysis patient wearing the belt in accordance with the present invention, showing the catheter secured and supported by the belt.

FIG. 1 of the drawings illustrates a peritoneal dialysis catheter support belt 1 in accordance with this invention. The belt is made of an elastic material and comprises an inner surface 3, an outer surface 5, a first end 7 and a second end 9. When worn by the dialysis patient, the belt 1 is positioned around the waist such that aperture 13 aligns directly with the exit site 17 of the catheter 19 on the patient's body, as best seen in FIG. 2. The catheter 19 enters aperture 13 at inner surface 3 and exits aperture 13 at outer surface 5. When a comfortable fit is established at exit site 17, first end 7 and second end 9 are secured by securing means 11, which can be self-securing means such as a hook and loop fastener or by other securing means such as garment snap(s) or button and button-hole fastener(s). As seen in Figure 3, the design of support belt 1 promotes ready access to the approximate position 21 along the waistline where first end 7 and second end 9 are reversibly secured. The dialysis patient can easily reach and manipulate the securing means 11 in order to fasten or unfasten the belt.

Reinforced aperture 13 provides direct support for catheter 19 at exit site 17 and properly aligns the catheter with holders 15. Thus, aperture 13 is instrumental in minimizing any discomfort at the exit site and promoting the desired security in the patient wearing the belt.

With further reference to FIG. 3, as the catheter 19 exits aperture 13, it is oriented by aperture 13 towards a plurality of holders 15, and is received by and supported by holders 15 along the length of catheter 19. Holders 15 are positioned immediately adjacent aperture 13 in order to ensure maximum support of the entire length of the catheter, and to minimize rotation of the catheter, which reduces any associated discomfort. The plurality of holders 15, attached to belt 1 at regularly spaced intervals along one portion of outer surface 5, is sufficient to accommodate varying lengths of catheters. In addition, holders 15 are made of an elastic material which allows belt 1 to accommodate any size catheter or medical tubing while holding it securely. The provision of a series of holders tends to disperse any pressure along the length of the belt, making wearing the belt more comfortable.

Belt 1 overlaps and protects exit site 17. It's snug fit allows for a wide range of activity and movement of the patient's body while providing assurance that the catheter will remain properly positioned at the site and supported against the body along its entire external length. In addition, belt 1 eliminates the skin irritation and discomfort associated with repeated application and removal of adhesive materials. The support belt 1 is also easily and economically manufactured, and it is conveniently washed and maintained for regular use.

It is therefore seen that a peritoneal dialysis catheter support belt may be provided which enables a patient to anchor and support a catheter without discomfort or fear of inadvertent dislodgement. As the above description is merely exemplary in nature, many variations will become apparent to those of skill in the art. Such variations, however, are included within the spirit and scope of this invention as defined by the following appended claims.

That which is claimed:

1. A belt for a peritoneal dialysis patient comprising:

an inner surface, an outer surface, a first end and a second end, said second end being reversibly securable to said first end;

an aperture defined by said belt;

a plurality of holders immediately adjacent said aperture along one portion of said outer surface;

wherein said belt secures and supports the entire external portion of a peritoneal catheter extending from an exit site on a patient's body, said aperture receiving and orienting said catheter toward said plurality of holders, said plurality of holders receiving and securing said catheter.

2. A belt for a peritoneal dialysis patient according to claim 1 wherein said aperture is reinforced.

3. A belt for a peritoneal dialysis patient according to claim 1 wherein said plurality of holders are permanently affixed to said belt.

4. A belt for a peritoneal dialysis patient according to claim 2 wherein said plurality of said holders accommodate various diameters and lengths of said catheter.

5. A belt for a peritoneal dialysis patient according to claim 1 wherein said belt is recloseable.

6. A belt for a peritoneal dialysis patient according to claim 1 wherein said second end is reversibly secured to said first end by a hook and loop fastener.

7. A belt for a peritoneal dialysis patient according to claim 1 wherein said belt is made of an elastic material.

8. A belt for a peritoneal dialysis patient according to claim 1 wherein said plurality of holders are constructed of an elastic material.

9. A belt for a peritoneal dialysis patient according to claim 1 wherein said plurality of holders are loops attached to said outer surface of said belt.

10. A recloseable catheter support belt for use by a peritoneal dialysis patient comprising:

an inner surface, an outer surface, a first end and a second end, said second end being reversibly secured to said first end;

an aperture defined by said belt;

a plurality of holders immediately adjacent said aperture along one portion of said outer surface;

wherein said belt extends around a mid-portion of said patient's body aligning said aperture of said belt with an exit site on said patient's body, said aperture receiving and orienting said catheter toward said plurality of holders, said plurality of holders receiving and securing said catheter.

\* \* \* \* \*